United States Patent [19]

Lysenko et al.

[11] Patent Number: 5,710,290

[45] Date of Patent: Jan. 20, 1998

[54] FUNCTIONALIZED CYCLOALIPHATIC NITRILE OXIDES

[75] Inventors: Zenon Lysenko; Clark H. Cummins, both of Midland, Mich.; Ramki Subramanian, Houston, Tex.; Richard F. Fibiger, Midland, Mich.

[73] Assignee: The Dow Chemical Company, Midland, Mich.

[21] Appl. No.: 734,291

[22] Filed: Oct. 21, 1996

[51] Int. Cl.$^6$ .................. C07D 303/38; C07C 13/10; C07C 13/18

[52] U.S. Cl. .................. 549/513; 549/546; 558/299

[58] Field of Search .................. 549/513, 546; 558/299

[56] References Cited

U.S. PATENT DOCUMENTS

| | | | |
|---|---|---|---|
| 2,996,556 | 8/1961 | Ilgenfritz et al. | 260/653.5 |
| 3,258,397 | 6/1966 | Hess et al. | 514/520 |
| 3,271,462 | 9/1966 | Earing et al. | 260/615 |
| 5,095,061 | 3/1992 | Chavez, Jr. et al. | |
| 5,342,541 | 8/1994 | Chavez, Jr. et al. | |

OTHER PUBLICATIONS

Griess, G. A., "Styrene Resins", Styrene: Its Polymers, Copolymers and Derivatives, pp. 811, 859–860 (1952).

Grundmann, Ch. et al., "The Nitrile Oxides: Versatile Tools of Theoretical and Preparative Chemistry", pp. 1–242 (1971).

March, Advanced Organic Chemistry, p. 826 (1992).

Yakubov, A. P. et al., "Synthesis of Stable Functionally Substituted Nitrile Oxides of the Aromatic Series". N. D. Zelinskii Institute of Organic Chemistry, Academy of Science of the USSR, Moscow. Translated from Izvestiya Akademii Nauk SSSR, Seriya Khimicheskaya, No. 5, pp. 1201–1203 (May 1991).

Yakubov, A. P. et al., "Synthesis of Sterically Hindered Aromatic Aldehydes", N. D. Zelinskii Institute of Organic Chemistry, Academy of Sciences of the USSR, Moscow. Translated from Izvestiya Akademii Nauk SSSR, Seriya Khimicheskaya, No. 7, pp. 1609–1615 (Jul. 1991).

Yakubov, A. P. et al., "Synthesis of Sterically Hindered Aromatic Dialdehydes", N. D. Zelinskii Institute of Organic Chemistry, Academy of Sciences of the USSR, Moscow. Translated from Izvestiya Akademii Nauk SSSR, Seriya Khimicheskaya, No. 7, pp. 1700–1703 (Jul. 1991).

Primary Examiner—C. Warren Ivy
Assistant Examiner—Lyman H. Smith
Attorney, Agent, or Firm—Reid S. Willis

[57] ABSTRACT

A suitably functionalized cycloaliphatic nitrile oxide can be used to convert unsaturated sites to alcohol or epoxy sites. The cycloaliphatic nitrile oxide may be useful in applications such as the preparation of polycarbonates, polyurethanes, or crosslinked polybutadiene, or poly(styrene-butadiene). The cycloaliphatic nitrile oxide is represented by the formula:

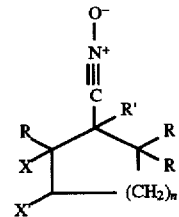

wherein R' and each R are independently hydrogen, $C_1$–$C_{12}$ alkyl, or halo; X and X' are independently hydrogen, halo, hydroxyl, or together with the carbon atoms to which they are attached form an epoxy group, with the proviso that at least one of X and X' is not hydrogen; and n is 1 or 2.

12 Claims, No Drawings

FUNCTIONALIZED CYCLOALIPHATIC NITRILE OXIDES

STATEMENT OF THE INVENTION

The present invention relates to a functionalized cycloaliphatic nitrile oxide, which can impart reactive functionality onto unsaturated systems.

BACKGROUND OF THE INVENTION

Polyols are hydroxy-functional chemicals or polymers covering a wide range of molecular weight, hydroxy functionality and composition. The predominant use of polyols such as poly(propylene oxide/ethylene oxide) (poly(PO/EO)) and poly(propylene oxide) (poly(PO)) based polyols is as a component in the manufacture of polyurethane or polyurea polymers or resins. They are also useful as components or intermediates for other polymers including polyesters and epoxy resins.

The polyol properties affect the properties of the polymers made using the polyol. For example, a flexible polyurethane foam is commonly made using linear or slightly branched polyols whereas a rigid polyurethane foam is made using branched polyols. In addition, the polyol functionality and primary hydroxyl content of the polyol affects its reactivity. The reactivity of a polyol toward urethane-forming reactants (for example, isocyanate-functional groups) is an important property which affects the resulting polymer properties as well as its processing. Other properties such as the viscosity, solubility, and stability of the polyols are also important.

In a typical process, the polyol is prepared by contacting an alkylene oxide such as ethylene oxide, propylene oxide, butylene oxide or mixtures thereof with an active hydrogen initiator, typically a polyhydric initiator such as glycerol, generally in the presence of a catalyst such as a base, for example, potassium hydroxide, or an amine. Following preparation, the reaction product is purified to reduce the catalyst level and other by-products. The resulting product is a polyol with predominantly hydroxyl end groups. However, propylene oxide can isomerize during reaction to give an allyl alcohol which may further undergo alkoxylation (for example, propoxylation); thereby resulting in a number of chains capped with terminal unsaturation, for example, propoxylated allyl alcohol which is monofunctional. This is particularly evident when a basic catalyst is employed.

Terminal unsaturation is undesirable in the preparation of polyurethanes, since the unsaturation is unreactive with the isocyanate functionality. The unreacted, particularly terminal, unsaturation is also susceptible to environmental influences and can adversely affect the properties such as compressive and tensile strengths, discoloration, flexural modulus and humid aging, of the resulting polymer. In particular, the modulus of a flexible polyurethane or polyurea foams or elastomeric polymers is reduced as the amount of unsaturation or monohydroxyl compound increases.

One reported method for reducing the unsaturation in a polyol composition is to treat the product of the reaction of the initiator and the alkylene oxide with an acid. (See, for example, U.S. Pat. Nos. 2,996,556 and 3,271,462.) However, the acid must be removed after treatment.

In yet another method for reducing the propenyl polyethers in hydroxy-functional polyethers, U.S. Pat. No. 5,095,061 teaches contacting a neutral polyol with an acid catalyst and water to convert the propenyl polyether to propionaldehyde, contacting the resulting product with an epoxy to scavenge the acid catalyst, and then removing the water and propionate. Similarly, U.S. Pat. No. 5,342,541 teaches contacting a polyether polyol with an acid ion exchange resin and water to convert the propenyl polyether to propionaldehyde, and then contacting the resulting product with an epoxy to reduce the acidity of the polyol. However, both the described processes involve additional steps such as the removal of acid.

It would be desirable to reduce the unsaturation, particularly the terminal unsaturation, of a polyol composition containing monoalcohols containing terminally unsaturated groups. It would further be desirable to increase the weight average molecular weight of a polyol composition.

SUMMARY OF THE INVENTION

In one aspect, the present invention is a compound represented by the formula:

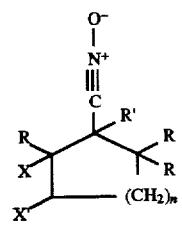

wherein R' and each R are independently hydrogen, $C_1$–$C_{12}$ alkyl, or halo; X and X' are independently hydrogen, halo, hydroxyl, or together with the carbon atoms to which they are attached form an epoxy group, with the proviso that not more than one of X and X' is hydrogen; and n is 1 or 2.

In a second aspect, the present invention is a process for preparing a functionalized cycloaliphatic nitrile oxide represented by the formula:

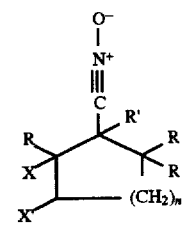

comprising the steps of:

(a) contacting an epoxide represented by the formula:

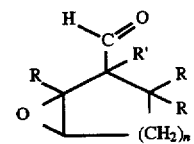

with a salt of hydroxyl amine under reaction conditions sufficient to form an aldoxime represented by the formula:

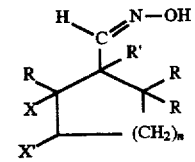

and (b) dehydrogenating the aldoxime to form the functionalized cycloaliphatic nitrile oxide;

wherein R' and each R are independently hydrogen, $C_1$–$C_{12}$ alkyl, or halo; X and X' are each independently hydroxy or halo, or together with the carbon atoms to which they are attached form an epoxy group, with the proviso that not more than one of X and X' is halo; and n is 1 or 2.

In a third aspect, the present invention is a process for converting an unsaturated monoalcohol to a polyol containing an isoxazoline group, comprising contacting the monoalcohol with a functionalized cycloaliphatic nitrile oxide under conditions suitable to form the polyol containing the isoxazoline group, wherein the cycloaliphatic nitrile oxide is represented by the formula:

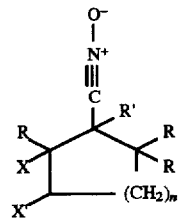

wherein R' and each R are independently hydrogen, $C_1$–$C_{12}$ alkyl, or halo; X and X' are each independently hydroxy or halo, or X and X' together with the carbon atoms to which they are attached form an epoxy group, with the proviso that at least one of X and X' is not halo; and n is 1 or 2.

The functionalized cycloaliphatic nitrile oxide of the present invention provides a flexible, economical means for providing reactive functionality, for example, an epoxy, hydroxy, or halo group, onto unsaturated systems. In particular, the functionalized cycloaliphatic nitrile oxide can provide an efficient means for preparing polyols from a monoalcohol having olefinic unsaturation. In the case where the functionalized cycloaliphatic nitrile oxide contains a crosslinker such as an epoxy group, concommitant removal of unsaturation along with the formation of a higher molecular weight polyol can be achieved, thereby providing desirably high monodispersity to the polymeric composition.

The polyol compositions are useful in the preparation of polymers formed from polyols, particularly in the preparation of polyurethanes.

DETAILED DESCRIPTION OF THE INVENTION

The compound of the present invention is a cycloaliphatic nitrile oxide represented by the formula:

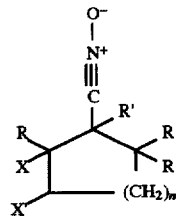

wherein R' and each R are independently hydrogen, $C_1$–$C_{12}$ alkyl, or halo; X and X' are each independently halo, hydroxyl, or together with the carbon atoms to which they are attached, form an epoxy group, preferably with the proviso that at least one of X and X' is not halo; and n is 1 or 2, preferably 2. Preferably, each R is independently hydrogen, methyl, ethyl, chloro, or bromo; more preferably ethyl or methyl, and most preferably methyl. Preferably, R' is hydrogen, methyl, or ethyl, more preferably hydrogen. Preferably, X and X' are each independently hydroxy, chloro, bromo, or together with the carbon atoms to which they are attached form an epoxy group. More preferably, one of X and X' is chloro, and the other of X and X' is hydroxy, or X and X' together with the carbon atoms to which they are attached form an epoxy group.

The functionalized nitrile oxide can be prepared, for example, from the corresponding functionalized aldehyde, which is represented by Formula (I):

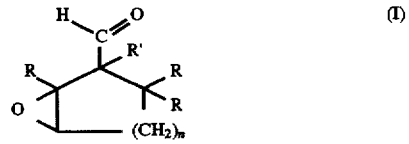

where R and R' are as previously defined. The functionalized aldehyde represented by Formula (I) can be converted first to the corresponding functionalized aldoxime by contacting the aldehyde with a hydrohalide salt of hydroxylamine under conditions suitable to form the aldoxime represented by Formula (IIa).

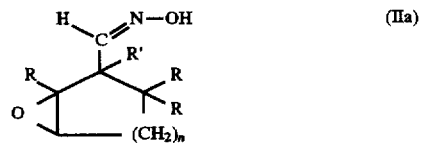

Preferably, the aldoxime is prepared in the presence of a buffer such as sodium or potassium acetate, and in a polar protic solvent such as a $C_1$–$C_4$ alcohol, more preferably ethanol or isopropanol. The reaction is preferably carried out at a temperatures above ambient temperature, more preferably under reflux conditions. If insufficient buffer is used, a halohydrin may be produced as a by-product; in the substantial absence of a buffer, the halohydrin can be exclusively produced. An example of a halohydrin is the chlorohydrin represented by Formula (IIb).

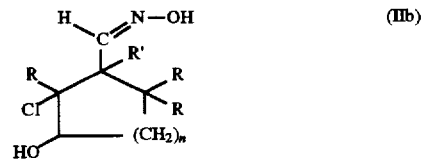

It is therefore preferred that a stoichiometric excess of the buffer with respect to the hydrohalide salt be used, more preferably not less than a 2-fold excess, if the epoxy functionality is desired, and no buffer be used if the halohydrin is exclusively desired.

The reaction may be monitored by any suitable analytical technique such as infrared spectroscopy, which can indicate the extent of completeness of the reaction by disappearance of an absorption band at about 1700 cm$^{-1}$, which corresponds to an aldehyde absorption, and the increase of an absorption band at about 1725 cm$^{-1}$, which corresponds to the aldoxime.

The functionalized aldoxime (either the epoxide or chlorohydrin or both) may be isolated by any suitable technique, such as extraction followed by drying over a drying agent, and converted to the desired functionalized nitrile oxide by contact with a hypohalite under conditions suitable to form the nitrile oxide. Preferably, the aldoxime is dissolved in a solvent that does not react with the hypohalite or with the aldoxime, more preferably a non-polar aprotic solvent, and contacted with an aqueous solution of sodium hypochlorite or sodium hypobromite, more preferably a stoichiometric excess of sodium hypochlorite or sodium hypobromite. The reaction is preferably carried out at subambient temperatures, more preferably not greater than about 15° C., most preferably not greater than about 5° C., and preferably not less than about −10° C., more preferably not less than about −5° C. As with the conversion of the aldehyde to the aldoxime, the conversion of the aldoxime to the nitrile oxide can be monitored by infrared spectroscopy by the disappearance of the absorption band at about 1725 cm$^{-1}$, and the appearance of a strong absorption band at 2300 cm$^{-1}$.

The functionalized cycloaliphatic aldehyde can be prepared by a multi-step method starting from a dienal such as a 2,5-heptadienal, a 2,5- or a 2,6-octadienal, or a 2,6-nonadienal or decadienal. Examples of suitable dienals include E,E-3,6,7-trimethyl-2,5-octadienal (Chem. Abstracts Reg. 142787-73-3), E,Z-3,6,7-trimethyl-2,5-octadienal (Chem. Abstracts Reg. 142787-79-9); E,E-3,7-dimethyl-2,6-nonadienal (Chem. Abstracts Reg. 121952-89-4); 7-isopropyl-3,8-dimethyl-2,6-nonadienal (Chem. Abstracts Reg. 106838-99-7); 3,7,8-trimethyl-2,6-nonadienal (Chem. Abstracts Reg. 105520-17-0); 7-chloro-3-methyl-2,6-octadienal (Chem. Abstracts Reg. 98959-16-1); 3,6-dimethyl-2,5-heptadienal (Chem. Abstracts Reg. 96839-90-6); Z-7-methyl-3-(1-methylethyl)-2,6-octadienal (Chem. Abstracts Reg. 84451-12-7); E-7-methyl-3-(1-methylethyl)-2,6-octadienal (Chem. Abstracts Reg. 84451-09-2); Z-3-ethyl-7-methyl-2,6-octadienal (Chem. Abstracts Reg. 74597-03-8); 3-ethyl-7-methyl-2,6-octadienal (Chem. Abstracts Reg. 74596-86-4); Z-2,3,6,7-tetramethyl-2,6-octadienal (Chem. Abstracts Reg. 73141-57-8); E-2,3,6,7-tetramethyl-2,6-octadienal (Chem. Abstracts Reg. 73141-56-7); E-2,3,7-trimethyl-2,6-octadienal (Chem. Abstracts Reg. 73141-53-4); E-3,7-dimethyl-2,6,-nonadienal (Chem. Abstracts Reg. 71073-15-8); Z-3,7-dimethyl-2,6,-nonadienal (Chem. Abstracts Reg. 71073-14-7); 3,7,9-trimethyl-2,6-decadienal (Chem. Abstracts Reg. 58605-97-3); 7-ethyl-3-methyl-2,6-nonadienal (Chem. Abstracts Reg. 53892-82-3); (Chem. Abstracts Reg. 41448-29-7); 3-ethyl-7-methyl-2,6-nonadienal (Chem. Abstracts Reg. 33661-45-9); E,Z-3,7-dimethyl-2,6-nonadienal (Chem. Abstracts Reg. 32775-54-5); E-3,6,7-trimethyl-2,6-octadienal (Chem. Abstracts Reg. 31187-17-4); Z-3,6,7-trimethyl-2,6-octadienal (Chem. Abstracts Reg. 31187-16-3); 7-methyl-3-propyl-2,6-octadienal (Chem. Abstracts Reg. 25578-44-3); 3-ethyl-7-methyl-2,6-octadienal (Chem. Abstracts Reg. 25578-42-1); 3,7-dimethyl-2,6-octadienal (citral), Chem. Abstracts Reg. 5392-40-5); 7-methyl-3-(1-methylethyl)-2,6-octadienal (Chem. Abstracts Reg. 2756-37-8); 3-isobutyl-7-methyl-2,6-octadienal (Chem. Abstracts Reg. 2756-36-7); 2,3,7-trimethyl-2,6-octadienal (Chem. Abstracts Reg. 1712-91-0); with 3,7-dimethyl-2,6-octadienal being more preferred.

In a preferred method of preparing the functionalized cylcoaliphatic aldehyde represented by Formula (I), the dienal is contacted with a primary amine, more preferably aniline in the presence of a catalytic amount of an acid such as p-toluenesulfonic acid, to form the corresponding Schiff base. The Schiff base can be cyclized to a cyclic enal by gradual addition to a molar excess of a strong acid such as sulfuric acid. The addition is preferably sufficiently gradual to maintain a substantial constancy of temperature of the reaction. This reaction is preferably carried out and maintained at a temperature not higher than 0° C., more preferably not higher than −10° C., and most preferably not higher than −20° C., and preferably not less than −40° C., and more preferably not less than −30° C., and most preferably not less than −25° C. The cyclic enal can then be epoxidized using reagents and reaction conditions well known in the art. (See March in *Advanced Organic Chemistry*, Wiley: New York, 1992, page 826 and references disclosed therein.) Preferably, the cyclic enal is epoxidized by a peracid, more preferably m-chloroperbenzoic acid, generally under mild conditions. The preferred method of preparing the functionalized cycloaliphatic aldehyde represented by Formula (I) is illustrated by the following reaction scheme.

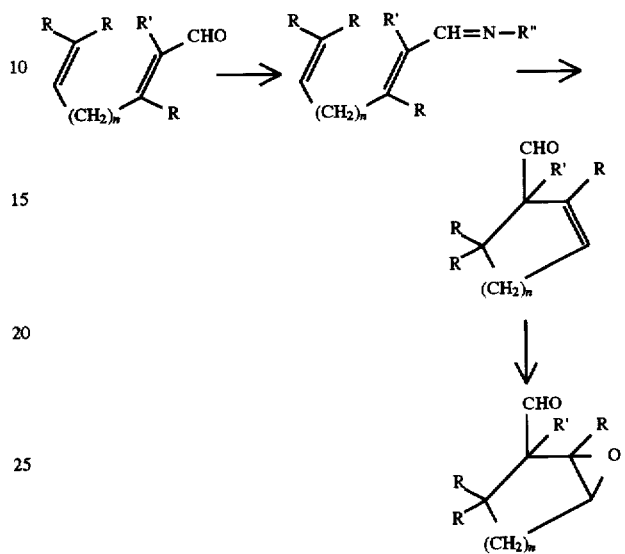

It is also possible to form a 2-hydroxy-2-alkyl-3-halo-cyclic-1-nitrile oxide in two steps from the aldoxime (IIa) by treating the aldoxime (IIa) with a strong protic acid, such as a hydrogen halide, and potassium oxymonosulfate (available as Oxone™, a trademark of E. I. Du Pont de Nemours) to form the corresponding oxaminoylhalide, followed by treatment with base such as a trialkylamine, more preferably triethylamine, according to the following scheme.

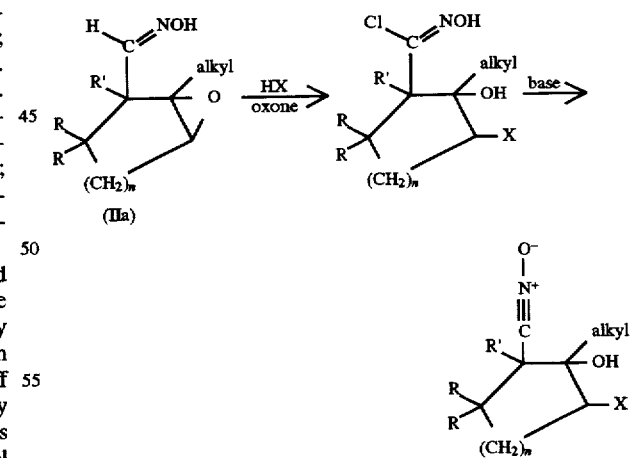

Cycloaliphatic nitrile oxides that contain monohalo, monohydroxy, dihalo, or dihydroxy groups may also be prepared by forming the aldoxime from the olefinic precursor to the epoxide, followed by halogenation, hydrohalogenation, or hydration using methods well known in the art of addition to multiple bonds:

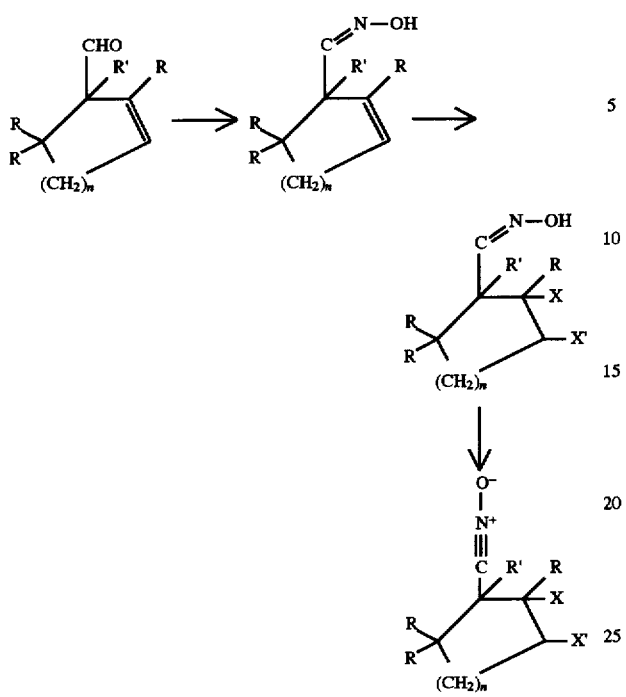

where X and X' are each independently H, halo, or hydroxy with the proviso that at least one of X and X' is not H.

The functionalized cycloaliphatic nitrile oxides of the present invention are preferably stable at room temperature indefinitely. Such nitrile oxides can be used to substitute unwanted unsaturated groups in a polyol composition with desirable functional groups such as epoxide groups or hydroxyl groups. The addition of a cycloaliphatic nitrile oxide containing an epoxide to a monoalcohol containing a terminal olefin group can readily convert the terminal olefin to an isoxazoline containing an epoxide and an OH group. The epoxide group can, for example, serve as a crosslinker to prepare a higher molecular weight polyol, or be hydrolyzed to form a triol, as illustrated:

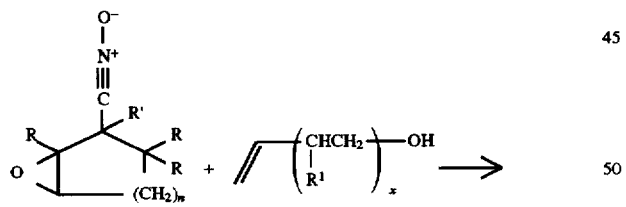

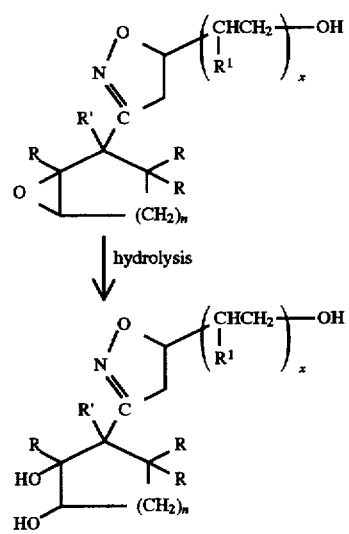

where $R^1$ is an alkyl group and x is an integer.

The functionalized cycloaliphatic nitrile oxide can also be used to impart crosslinking functionality onto an unsaturated polymer such as a polybutadiene or a poly(butadiene-styrene), preferably polybutadiene or poly(butadiene-styrene) which contain at least some fraction of the more highly readily crosslinkable geminal or terminal olefin groups.

The reaction occurs with no evolution of by-products, and preferably at ambient temperature. The suitably functionalized cycloaliphatic nitrile oxide may be particularly preferred in cases where photolytic stability of the polymer is critical.

The following example is for illustrative purposes only and is not intended to limit the scope of this invention. All percentages are by weight unless otherwise specified.

EXAMPLE 1

Preparation of Functionalized Stable Cycloaliphatic Nitrile Oxides

Reaction Scheme:

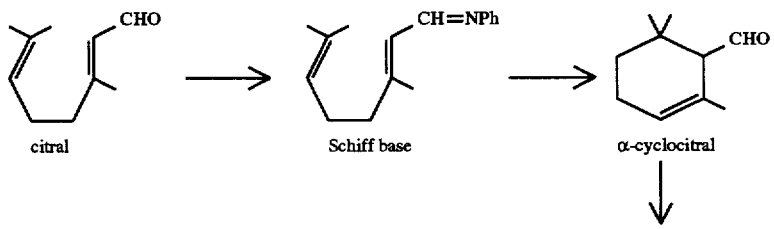

-continued

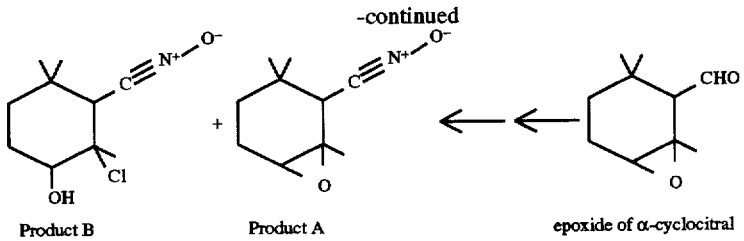

Product B     Product A     epoxide of α-cyclocitral

To a solution of citral (30.6 g, 0.2 mole) in toluene (150 mL) is added aniline (18.6 g, 0.2 mole) along with a catalytic amount of p-toluenesulfonic acid (a pinch). The reactants are stirred at room temperature for about 2 hours. The colorless mixture of citral and aniline turn yellow upon stirring and water that is produced in the reaction separates out. The mixture is washed with aqueous sodium bicarbonate solution, dried over anhydrous sodium sulfate and the toluene removed by rotary evaporation. The Schiff base is obtained in pure form by Kugelrohr distillation (around 140° C. at 0.25 mm Hg) as a light-yellow oil in about 75 percent yield (32.5 g).

A solution of the Schiff base (32.5 g, 0.143 mole) in diethyl ether is added dropwise over 3 hours to a flask containing an 18.7 molar excess of sulfuric acid (266 g, 2.72 mol). The flask is equipped with a mechanical stirrer, a gas inlet, and a dry ice/perchloroethylene bath. The reaction is stirred vigorously under a constant purge of nitrogen, and maintained at −20° C. to −25° C. throughout the course of the addition. After the addition of the Schiff base is complete, the mixture is stirred under nitrogen for 3 hours at −15° C. The mixture is then poured onto crushed ice, taking care that the temperature does not rise above 0° C. until after the addition is complete. The temperature of the quenched solution is allowed to rise to about 15° C., whereupon the organic product is extracted several times with ether, and the combined ether extracts are dried over anhydrous magnesium sulfate. Removal of the ether by rotary evaporation followed by Kugelrohr distillation (around 60° C. at 0.25 mm Hg) gives about a 60 percent yield (13.0 g) of cyclocitral (around 95 percent a and 5 percent b).

The corresponding epoxide of the cyclocitral is prepared by adding dropwise a 1.5-fold molar excess of m-chloroperbenzoic acid in chloroform to a solution of the cyclocitral in methylene chloride. The mixture is stirred and after some time m-chlorobenzoic acid precipitates out as a white fluffy powder. The mixture is stirred at room temperature until GC analysis indicates less than 0.1 percent cyclocitral. The mixture is filtered, the excess m-chloroperbenzoic acid is quenched with 10 percent $Na_2SO_3$ solution, and the organic product is extracted with chloroform. The product is purified by Kugelrohr distillation (about 45° C. at 0.3 mm Hg) to give about a 95 percent yield of the epoxide.

A 3-necked flask fitted with a condenser and stirrer is charged with a solution of the epoxide (4.58 g, 0.027 mole) in ethanol, hydroxylamine hydrochloride (1.88 g, 0.027 mol) and sodium acetate (2.21 g, 0.027 mole). The solution is heated to reflux for 2 hours, allowed to cool, then poured into 100 mL of water. The organic product is extracted with ether. Evaporation of the ether (after drying the organic layer over anhydrous magnesium sulfate) yields a viscous yellow oil from which white crystals of the oxime separate out. The crystals are filtered, washed with hexane and dried in vacuo.

Bleach (50 mL of a 10 percent solution in water) is added to a solution of the oxime in methylene chloride (20 mL) maintained at 0° C. The mixture is stirred for about 1.5 hours, whereupon the organic layer is separated and the aqueous layer is further extracted with methylene chloride. The combined organic layers are washed with water and dried over anhydrous magnesium sulfate. The solvent is then evaporated to yield a yellow oil which is about a 50:50 mixture of 1a,3,3-trimethylperhydrobenzo[b]oxirene-2-nitrile oxide (Product A) and 2-chloro-3-hydroxy-2,6,6-trimethylcyclohexane-1-nitrile oxide (Product B). The product is characterized mainly by IR spectroscopy (the IR spectrum of the nitrile oxide is very distinct in that it has an intense band at around 2300 $cm^{-1}$).

What is claimed is:

1. A compound represented by the formula:

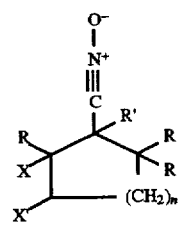

wherein R' and each R are independently hydrogen, $C_1$–$C_{12}$ alkyl, or halo; X and X' are independently hydrogen, halo, hydroxyl, or together with the carbon atoms to which they are attached form an epoxy group with the proviso that not more than one of X and X' is hydrogen; and n is 1 or 2.

2. The compound of claim 1 wherein each R is independently hydrogen, methyl, ethyl, chloro, or bromo; R' is hydrogen, methyl, or ethyl; X and X' are each independently hydroxy, chloro, bromo, or together with the carbon atoms to which they are attached form an epoxy group.

3. The compound of claim 2 wherein one of X and X' is chloro or bromo, and the other of X and X' is hydroxy, or X and X' together with the carbon atoms to which they are attached, form an epoxy group; R is methyl or ethyl; and R' is hydrogen.

4. The compound of claim 2 wherein X is chloro, X' is hydroxy, and n is 2.

5. The compound of claim 2 wherein X is chloro and X' is hydroxy.

6. A process for preparing a functionalized cycloaliphatic nitrile oxide represented by the formula:

comprising the steps of:

(a) contacting an epoxide represented by the formula:

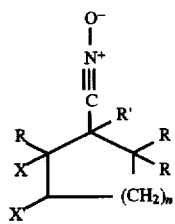

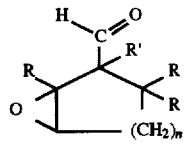

with a salt of hydroxyl amine under reaction conditions sufficient to form an aldoxime represented by the formula:

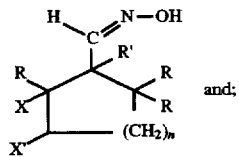

(b) dehydrogenating the aldoxime to form the functionalized cycloaliphatic nitrile oxide;
wherein R' and each R are independently hydrogen, $C_1$–$C_{12}$ alkyl, or halo; X and X' are each independently hydroxy or halo, or together with the carbon atoms to which they are attached form an epoxy group; and n is 1 or 2.

7. The process of claim 6 wherein the epoxide is contacted with hydroxylamine hydrochloride and a stoichiometric excess of sodium acetate with respect to the hydroxylamine hydrochloride under conditions of reflux in a $C_1$–$C_4$ alcohol.

8. The process of claim 7 wherein the dehydrogenation is carried out by contacting the aldoxime with an alkali metal hypohalite.

9. The process of claim 8 wherein each R is independently hydrogen, methyl, ethyl, chloro, or bromo; and R' is hydrogen, methyl, or ethyl.

10. The process of claim 9 wherein one of X and X' is chloro or bromo, and the other of X and X' is hydroxy, or X and X' together with the carbon atoms to which they are attached form an epoxy group; R is methyl or ethyl; R' is hydrogen; and n is 2.

11. A process of converting a monoalcohol having unsaturation to a polyol containing an isoxazoline group, comprising contacting the monoalcohol with a functionalized cycloaliphatic nitrile oxide under conditions suitable to form the polyol containing the isoxazoline group, wherein the cycloaliphatic nitrile oxide is represented by the formula:

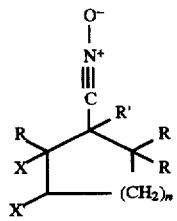

wherein R' and each R are independently hydrogen, $C_1$–$C_{12}$ alkyl, or halo; X and X' are each independently hydroxy or halo, or X and X' together with the carbon atoms to which they are attached form an epoxy group, with the proviso that at least one of X and X' is not halo; and n is 1 or 2.

12. The process of claim 11 wherein each R is independently methyl or ethyl; R' is hydrogen; X is chloro and X' is hydroxy.

* * * * *